US005118779A

United States Patent [19]

Szycher

[11] Patent Number: 5,118,779

[45] Date of Patent: Jun. 2, 1992

[54] HYDROPHILIC POLYURETHANE ELASTOMERS

[75] Inventor: Michael Szycher, Lynnfield, Mass.

[73] Assignee: PolyMedica Industries, Inc., Woburn, Mass.

[21] Appl. No.: 419,452

[22] Filed: Oct. 10, 1989

[51] Int. Cl.[5] ........................ C08G 18/67; C08F 2/46; C08J 3/28, A61K 41/00

[52] U.S. Cl. ........................ 528/75; 528/904; 526/301; 525/920; 522/34; 522/39; 522/42; 522/90; 424/401; 424/435; 424/443; 424/448; 424/449

[58] Field of Search ........................ 522/90, 34, 39, 42; 424/443, 449, 435, 448, 401; 528/75, 904; 525/920; 526/301

[56] References Cited

U.S. PATENT DOCUMENTS

| | | | |
|---|---|---|---|
| 3,943,045 | 3/1976 | Cordrey et al. | 424/443 |
| 4,188,455 | 2/1980 | Howard | 525/920 |
| 4,192,762 | 3/1980 | Osborn | 528/75 |
| 4,221,646 | 9/1980 | Finelli et al. | 528/67 |
| 4,248,958 | 2/1981 | Faust | 522/78 |
| 4,267,295 | 5/1981 | Gallop et al. | 526/301 |
| 4,751,273 | 6/1988 | Lapin et al. | 526/301 |
| 4,810,582 | 3/1989 | Gould et al. | 424/443 |
| 4,908,297 | 3/1990 | Head et al. | 522/97 |
| 4,940,737 | 7/1990 | Braatz et al. | 528/904 |
| 4,968,725 | 11/1990 | Mukai et al. | 522/90 |

*Primary Examiner*—John Kight, III
*Assistant Examiner*—Rabon A. Sergent
*Attorney, Agent, or Firm*—Morgan & Finnegan

[57] ABSTRACT

A non-toxic hydrophilic polyurethane elastomer having less than about 0.5% by weight extractables and which is curable in the absence of heat is disclosed. The elastomers are prepared from suitable hydrophilic polyurethane oligomers in combination with suitable ultraviolet light absorbers which become chemically bound into the elastomer during the polymerization (curing) thereof and thus become essentially non-extractable therefrom.

48 Claims, No Drawings

HYDROPHILIC POLYURETHANE ELASTOMERS

BACKGROUND OF THE INVENTION

This invention relates to non-toxic hydrophilic polyurethane elastomers which are intended to come into contact with tissue and/or fluids of a living body. Particularly, it relates to polyurethane elastomers which are hydrogels, i.e. materials which exhibit the ability to swell in water and retain greater than about 20 weight percent of water within their structures while being water-insoluble. Still more particularly, the polyurethane elastomers can be cured non-exothermically and after curing contain less than about 0.5% extractables. More particularly, it relates to the use of such materials as matrices from which medications, particularly water-soluble medications, can be released predictably over a prolonged period of time through the skin or mucosa of a patient. Still more particularly, it relates to elastomers prepared from polyurethane oligomers, which are fluid at room temperature, in combination with a photoinitiator which contains at least one chemical group which will enable the absorber to become chemically bound into, and thus not extractable from, the cured elastomer after exposure to actinic radiation. Still more particularly, this invention relates to incorporating a medication into the polyurethane oligomer photoinitiator composition and polymerizing the fluid composition by exposing it to ultraviolet light at about room temperature to yield a controlled delivery system for hydrophilic, hydrophobic, lipophilic, lipophobic, as well as insoluble materials which is non-toxic to humans and which also avoids exposure of the medication to elevated temperatures.

In the preparation of any material intended for use in contact with or inside a living body, it is self-evident that the materials must be non-toxic. Thus if a toxic ingredient has been used in preparing such materials, it must be either totally removed or rendered non-toxic before actual use. In the manufacture of acrylic contact lenses, for instance, toxic initiators which are necessary for the polymerization reaction to occur can be and are removed before use, generally by extended and expensive, i.e. for 24 hours or more, leaching. In such systems avoidance of leaching procedures or similar operations to overcome the toxicity problem would clearly be desirable.

Such systems can not be used to deliver water-soluble medications by incorporating a medication therein, since any type of leaching procedure would of necessity remove the desired water-soluble medication at the same time it removed the undesired toxic component. As a result, presently available controlled delivery systems have been limited to the delivery of water-insoluble or substantially water-insoluble medications. The lack of a suitable hydrophilic delivery system which is simultaneously non-toxic and does not use heat in its formation has precluded the use of controlled delivery systems with water-soluble medications.

Current commercially available hydrogels generally fall into six general categories: poly(hydroxyalkyl methacrylates); polyacrylamides, polymethacrylamides and derivatives; poly(N-vinyl-pyrrolidone); anionic and cationic hydrogels; polyelectrolyte complexes; and polyvinyl alcohols. These materials suffer from a common problem: a lack of sufficient mechanical strength for many uses. This is especially a problem as the equilibrium water content within the three dimensional networks of covalently or ionically crosslinked hydrophilic polymers reaches 10% or higher due to swelling from interaction with aqueous solutions. As the water contents increase, the hydrogels become weaker and are easily torn. This low strength makes them unsuitable for applications in which they would be subjected to mechanical stress or abrasion.

Moreover, when dry several of the prior hydrogels are exceptionally brittle, necessitating their continual storage in an aqueous environment. In the case of contact lenses, this is advantageous since it renders the lenses ready for use. But the water storage also precludes the incorporation of medications into contact lenses since the medication would dissolve into the water during storage. While the brittleness problem could be solved by adding a suitable plasticizer, this would likely render the materials toxic due to the extractability of the plasticizer.

There is thus a need for an elastomeric hydrophilic polymer which is curable non-exothermically and which contains less than about 0.5 weight % of total extractables as prepared, i.e. without having to perform a leaching-type procedure. There is also a need for a material having the following combination of properties: elastomeric to be able to conform to any desired shape, sufficiently hydrophilic to be capable of absorbing water and water-soluble materials, non-toxic to man or animal, capable of releasing the water and water-soluble materials, liquid or at least flowable at close to room temperature before polymerization, and polymerizable to a solid form without heat.

U.S. Pat. No. 4,614,787 discloses a drug dispensing wound dressing based upon an actinic radiation curable polyurethane polymer matrix which is a reaction product of isophorone diisocyanate, a macroglycol which is preferably polypropylene glycol, and a chain terminator. The patent teaches: "Other high molecular weight glycols, such as polyethylene glycol (PEG) may be employed, but PEG is a solid at room temperature and a feasible rate of reaction would require heating." It uses ultraviolet photosensitizers, such as benzophenones, which are extractable from the final cured compositions, to effect curing. It also must be noted that wound dressings are intended for use in a physiologically unique environment in regard to the general delivery of drugs through intact skin since plasma exudate inherent from a wound will absorb any lipophilic compounds and carry them into a body extremely rapidly. However, the drug dispensing wound dressings disclosed would be inoperative in the absence of the exudate from an open wound, and, due to the presence of the extremely toxic benzophenone-type photosensitizers used in preparing the wound dressings, they would not be considered safe for use by various government regulatory agencies, e.g. the U.S. Food and Drug Administration. Also, the wound dressings contain several percent toxic extractables from the photosensitizers.

Similarly, U.S. Pat. No. 4,483,759 discloses an actinic radiation cured polyurethane acrylic copolymer containing toxic benzophenone-type photosensitizers. As such, the copolymers contain several percent toxic extractables and are not considered safe for human use.

U.S. Pat. No. 4,300,820 discloses a water absorptive composition capable of absorbing more than 45% of its weight of water and comprised of a vinyl lactam polymer or copolymer in combination with a water-insoluble copolymer. The blend of the two polymers is intended to control the equilibrium water content since the greater the amount of the insoluble polymer, the lower the water content.

U.S. Pat. No. 3,996,934 discloses a medical bandage having a reservoir of a drug within a wall member formed from a drug release rate controlling material which is permeable to the passage of the drug. The patent operates on different principles than does the present invention and does not suggest the use of ultraviolet light curing systems.

U.S. Pat. No. 3,975,350 discloses hydrophilic or hydrogel carrier systems such as coatings, body implants and other articles. While the articles which are produced contain essentially no extractables, they are NCO-terminated resins which are cured by the use of extended heat, i.e. 100° C. for about 48 hours, conditions which would be harmful to many drugs. No room temperature polymerizing systems are possible with the polymer systems disclosed.

Accordingly, there is a need for an elastomeric hydrophilic polymer which is both non-toxic and polymerizable in the absence of heat. It is an object of the present invention to provide such a material.

It is a further object of the invention to produce an elastomeric hydrogel containing substantially no extractables and which will cure upon exposure to ultraviolet radiation for a period of less than about two minutes.

It is a still further object of the present invention to provide a material which is strong yet flexible and which can be conformed to curved, flat as well as angular shaped bodies without cracking or other similar damage occurring.

These and still further objects and features of the present invention will be understood by those skilled in the art from a reading of the following detailed description of the invention.

SUMMARY OF THE INVENTION

The present invention is directed to a hydrophilic polyurethane elastomer which is polymerizable in the substantial absence of heat and, after polymerization, contains less than about 0.5% extractables. More particularly, the invention is directed to a urethane prepolymer system comprising an oligomer which is a reaction product of a diisocyanate, a bifunctional component having at least one active hydrogen on each terminal group and at least a portion of which is poly(ethyleneoxide), and a chain capping monomer, in combination with a photoinitiator which contains a chemical group which is reactive with a group on the chain capping monomer. Still more particularly, this invention is directed to the incorporation of medication into a composition of the liquid oligomer and the photoinitiator and curing (polymerizing) the oligomer to form a hydrophilic polyurethane elastomer which will controllably release the medication into a patient through its skin or mucosa, i.e. a drug delivery system, at a controlled rate.

DETAILED DESCRIPTION OF THE INVENTION

The hydrophilic polyurethane elastomers of the present invention having less than about 0.5, preferably less than about 0.3, and most preferably less than about 0.1% extractables and polymerizable non-exothermically are prepared by (i) combining a liquid polyurethane oligomer prepared by reaction of an aliphatic diisocyanate and a poly(ethyleneoxide)-containing compound having two terminal groups each of which contains an active hydrogen with a photoinitiator and (ii) subjecting the combination to actinic radiation to cure or polymerize the prepolymer. The oligomers useful herein may have any desired specific internal structure provided that the final elastomer contains at least about 5 weight percent poly(ethyleneoxide) groups, i.e. $-(CH_2CH_2O)-$, such that after polymerization a hydrophilic, elastomeric, water-insoluble polyurethane is produced. The oligomers are fluid or at least flowable, i.e. have viscosities below about 60,000 centipoise, at room temperature or only slightly above since this facilitates incorporation therein of the photoinitiator as well as any medication or other desired additives. More desirably, oligomers having a viscosity of less than about 40,000, preferably less than about 30,000, and most preferably less than about 20,000, centipoise at room temperature are used. If the viscosity of the oligomer is above about 40,000 centipoise at room temperature, then it may need to be heated somewhat, i.e. up to about 50° C., to facilitate mixing with the photoinitiator.

The oligomers useful in the present invention are comprised of a diisocyanate, a poly(ethyleneoxide)-containing component having at least one active hydrogen on each of two terminal groups, and a chain capping monomer.

The diisocyanates useful herein may be represented by the formula OCN—R—NCO wherein R is aliphatic including alicyclic compounds such as aliphatic, aliphatic-alicyclic and aliphatic-aromatic hydrocarbon compounds containing about from 4 to 26 carbon atoms, but more conventionally about from 6 to 20, and generally about from 6 to 13 carbon atoms. Representative examples of the above diisocyanates include: tetramethylene diisocyanate, hexamethylene diisocyanate, trimethyl-hexamethylene diisocyanate, dimer acid diisocyanate, isophorone diisocyanate, hydrogenated diphenylmethane diisocyanate, methylene di(cyclohexyl isocyanate), metaxylene diisocyanate, diethylbenzene diisocyanate, decamethylene 1,10-diisocyanate, cyclohexylene 1,2-diisocyanate, and cyclohexylene 1,4-diisocyanate.

Aliphatic diisocyanates are used because, as shown below, aromatic diisocyanates have been found to produce oligomers which are not sufficiently liquid at room temperature and thus would have to be heated substantially to be able to incorporate the photoinitiator and other additives. Moreover, aromatic diisocyanates have been found to absorb so much ultraviolet radiation that they are very slow polymerizing, requiring several minutes of radiation to yield only very thin films, i.e. less than about 0.005". While some aliphatic diisocyanates do yield oligomers requiring some slight warming to maintain liquidity, they have been found to not overly absorb ultraviolet radiation so that thick films, i.e. up to 0.030", polymerize within two minutes of exposure to ultraviolet light. Mixtures of two or more diisocyanates may also be used. The most preferred diisocyanates include isophorone diisocyanate and trimethylhexamethylene diisocyanate since they have been found to produce low viscosity oligomers which cure in less than about one minute of ultraviolet exposure.

The bifunctional component contains two terminal groups each having an active hydrogen which is reactive with an NCO group of the diisocyanate. The component further contains at least some poly(ethyleneoxide) groups, i.e. $-CH_2CH_2O-$. The two terminal groups of the component may be any groups which contain at least one active hydrogen. Thus suitable terminal groups include hydroxyl, amine, mono-substituted amine, carboxylic acid, aldehyde, and the like. Preferably the terminal groups are either hydroxyl or amine. Most preferably the terminal groups are hydroxyl and the component comprises a polyethylene glycol. Poly(ethyleneoxide)-containing bifunctional components useful herein generally have molecular weights ranging from about 500 to less than about 3000, preferably about 750 to 2500, and most preferably about 900 to 1500 Daltons. Generally as the molecular weight of the component increases, the resultant elastomer becomes softer, has a higher elongation, and is less resilient. Thus lower molecular weight materials are generally preferred. The poly(ethyleneoxide)-containing material not only provides hydrophilicity to the polyurethane elastomer but also, surprisingly, accelerates the cure. The balance of this component, if any, may be another macroglycol such as polypropylene glycol, polybutylene glycol, polytetramethylene ether glycol, polyethylene adipate glycol, polyhexamethylene carbonate glycol, and the like. Alternatively diamines, dicarboxylic acids, dialdehydes, such as hexyldiamine, octyldiamine, oleic acid, stearic acid, decyldialdehyde, octadecyldialdehyde and the like may be used. Still further alternatively, compounds having two different terminal groups containing active hydrogens, such as octyl-1-ol-8-amino, decyllol-10-amino, and the like may be used. Mixtures of different bifunctional compounds may also be used. Most useful herein are mixtures of poly(ethyleneoxide)-containing materials with other bifunctional compounds having two terminal groups containing active hydrogens (which will be reactive with the NCO groups of the diisocyanates) so as to control the hydrophilicity of the resultant elastomer.

The chain capping monomer useful herein contains an active hydrogen group, such as a hydroxyl, amine, carboxylic acid, or aldehyde group, which is reactive with the diisocyanate and a terminal vinyl group to subsequently be polymerized and thus cure the oligomer into an elastomeric body after an addition of a photoinitiator and exposure of the mixture to ultraviolet radiation. The chain capping monomer is preferably an acrylic compound such as hydroxyethyl acrylate or hydroxyethyl methacrylate because of its reactivity and hydrophilicity. Hydroxyethyl methacrylate (HEMA) is most preferred.

To prepare the oligomer, the diisocyanate, the bifunctional poly(ethyleneoxide)-containing component, and the chain capping monomer are reacted in approximately stoichiometric amounts, i.e. in the approximate ratio of 2 moles (2.0 equiv.) diisocyanate to 1 mole (1.0 equiv.) bifunctional poly(ethyleneoxide)-containing component to 2 moles (1.0 equiv.) chain capping monomer. While the oligomer may be prepared in a single reaction of the three reactants, it will more preferably be prepared by prereacting the diisocyanate and the bifunctional poly(ethyleneoxide)-containing component to form a prepolymer which is then reacted with the chain capping monomer. After which, the free isocyanate content is monitored by such as infrared spectroscopy and, if necessary, small amounts of the chain capping monomer added to scavenge any remaining isocyanate groups. An antioxidant such as tetrakis[methylene(3,5-ditert-butyl-4-hydroxyhydrocinnamate)] may be added to inhibit spontaneous oxygen-initiated curing. A conventional polyurethane catalyst such as dioctyl tin dilaurate, N-methyl morpholine, trimethylamine, triethylamine, zinc octoate, or dibutyl tin dilaurate is added to the reaction mediums in conventional amounts, i.e. about 0.2% or less.

To prepare the hydrophilic polyurethane elastomers of this invention, a photoinitiator containing a vinyl group which will copolymerize with the vinyl group of the chain capping monomer is uniformly mixed into the oligomer. Suitable photoinitiators are generally soluble in the oligomer so that they can be readily uniformly distributed therein and thus produce a complete cure. While the photoinitiator may contain more than one vinyl group, this is not preferred since it could make the compound too reactive and/or cause undesired crosslinking or chain extension which would result in a brittle and inelastic polymer. Generally the photoinitiator will be used in amount of about 0.5 to about 5, preferably about 1 to about 2, weight percent based on the weight of the oligomer. Suitable photoinitiators for use herein include benzil ketals, benzoin ethers, and aromatic ketones which have been modified to contain a polymerizable vinyl group. A photoinitiator containing a hydroxyl group and a vinyl group can be used. Such compounds may be prepared, for example, by acrylating a hydroxyethoxyphenylketone photoactive compound. Specific examples of preferred photoinitiators include (i) 4-(2-acryloyloxyethoxy)-phenyl-2-hydroxy-2-propylketone, (ii) 4-[2-(3-triethoxysilylpropoxy)]phenyl-2-hydroxy-2-propylketone, (iii) 4-(2-azidoethoxy)-phenyl-2-hydroxy-2-propylketone, (iv) 4-(2-aminoethoxy)phenyl-2-hydroxy-2-propylketone, and the like. A most preferred photoinitiator is 4-(2-acryloyloxyethoxy)-phenyl-2-hydroxy-2-propylketone, which may be prepared by reacting phenoxyethanol with isopropanol acid chloride (in the presence of anhydrous aluminum chloride and methylene chloride solvent) to form 4-(2-hydroxyethoxy)phenyl-2-hydroxy-2-propylketone via a Friedel-Krafts acylation. The propylketone is then reacted with acryl acid chloride and 2,4,6-trimethylpyridine in the presence of 4-methoxyphenol as a polymerization inhibitor. This propylketone is normally a relatively poor (slow) photoinitiator, but, as shown below, it has been found to be a particularly effective copolymerizing photoinitiator when used with the poly(ethyleneoxide)-containing oligomers of the present invention, particularly as opposed to essentially similar oligomers which contain poly(propyleneoxide) groups in place of the poly(ethyleneoxide) groups.

The oligomer-photoinitiator composition may then be formed into a desired shape by such as drawing, rolling, casting, or spraying using techniques well known in the art. The oligomer having the desired shape is then polymerized (cured) in situ by exposing it to ultraviolet radiation, typically between about 219 and 425 nm at 0.5 W/cm$^2$. The curing, which does not require the use of heat and is normally performed at room temperature, transforms the fluid oligomer into a solid hydrophilic, polyurethane elastomer.

When the hydrophilic polyurethane elastomer is used as a delivery system for medications, the medication will normally be added to the liquid oligomer along with the photoinitiator before the shape forming and exposure to ultraviolet radiation. The particular elastomer composition used for a specific medication must be chosen based upon knowledge of the heat sensitivity of the medication, i.e. the oligomer used must be one which is sufficiently liquid to allow uniform mixing therebetween at a low enough temperature so that the medication is not harmed. Therefore, the oligomers of this invention which are liquid at room temperature, such as those made from 2,4,4-trimethylhexamethylene diisocyanate, are most preferred for the delivery of most medications. The particular elastomer composition is also dependent upon the hydrophilic-hydrophobic and lipophilic-lipophobic balances of the particular medication, the delivery rate which is desired, and the time period during which the delivery is to continue.

The amount of $—CH_2CH_2O—$ groups, which may range from about 5 to about 85% by weight of the final elastomer, will depend upon the particular use to be made of the elastomer. If the elastomer is intended to be part of a drug delivery system for extremely hydrophilic drugs, the amount of $—CH_2CH_2O—$ groups will normally be quite high, i.e. 50 or more percent. But if the drug is hydrophobic the amount will generally be low. As a result, elastomers of this invention may be designed to deliver a medication at almost any essentially constant rate desired. The medications may be hydrophilic, hydrophobic, lipophilic, lipophobic, or even insoluble.

As a result of the variability of hydrophilicity levels of the present elastomers, any medication be it water-soluble or not, may be incorporated into an elastomer and that elastomer then used to deliver the medication to a patient through the skin or mucosa thereof. Suitable medications include, for example, pharmaceuticals, bacteriostats, viruscides, antibiotics, antifungal agents, topical anaesthetics, growth factors, skin softeners, anti-acne medications, external anaesthetics, cosmetics, and the like. Normally, a dispersion of the medication at an appropriate concentration is intimately blended into the oligomer-photoinitiator composition and the mixture exposed to ultraviolet radiation to cure the oligomer and form the structure which will retain and deliver the medication. The medication is released from the elastomeric structure at a controlled, sustained rate while the balance thereof yet to be released is protected by the structure.

To form a drug delivery system with the hydrophilic polyurethane elastomers containing the desired medication(s), the oligomer-photoinitiator-medication composition will usually be cast into a film of the appropriate thickness, i.e. at least about 0.010" and more preferably about 0.010" to about 0.040" so that a substantial quantity of the medication can be present, and then cured by exposure to ultraviolet radiation. The elastomers generally are able to contain aqueous solutions in amounts up to about their weight percent of $—CH_2CH_2O—$ groups. A pressure-sensitive adhesive conventionally used for bandages and the like may be used to attach the cured medication-containing film to a backing material and then a release paper or plastic film applied over the exposed surface of the adhesive and the film.

Other uses for the hydrophilic polyurethane elastomers in which they will be in contact with body fluids and/or tissue of living animals include wound dressings, catheter coatings so that they will be more blood compatible than currently available coatings and also easier to insert and remove from the body, mammary prostheses, and other chronic implantable prostheses. In each of these cases, the oligomers prepared as described are used in conventional manners, with the direct substitution of the present hydrophilic elastomers for the conventional materials.

The following examples are presented in illustration of the present invention and not in limitation thereof. All parts and percents are by weight unless otherwise specified.

EXAMPLE I

A four liter reactor equipped with continuous nitrogen blanketing and a heating mantel is charged with 198.26 g trimethylhexamethylene diisocyanate (TDMI) (2.0 equiv.), 500 g of polyethylene glycol having a molecular weight of 1000 (1.0 equiv.), and 0.0035% (based on the total weight) dioctyl tin dilaurate (Cotin 430 of Cosan Chemical Co.). Agitation is begun and the mixture is raised to and maintained at 60° C. After three hours, 125.64 g hydroxyethyl methacrylate (2.0 equiv.) and an additional 0.0035% of dioctyl tin dilaurate are added. The mixture is allowed to react exothermally to 110° C. for two hours.

At the completion of the oligomer-forming reaction, free isocyanate is monitored by infrared spectrophotometry, and if necessary small amounts of hydroxymethyl methacrylate are added (up to about 2 g) to scavenge any remaining isocyanate.

The oligomer is then cooled, filtered to remove impurities, and either stored in a plastic container for subsequent use or cured. The oligomer has a room temperature viscosity of 10,000 centipoise as determined by Brookfield viscosimeter. To cure the liquid oligomer, 3% of 4-(2-acryloyl-oxyethoxy-)-aryl-2-hydroxy-2-propylketone (AHPK, a photoinitiator having one polymerizable vinyl group) is added, the mixture agitated and deaerated. A 0.030" film of the resulting mixture is cast onto release paper and is exposed to ultraviolet radiation between 219 and 380 nanometers for 20 seconds at 0.5 $W/cm^2$.

The result is a fully cured water-insoluble, hydrophilic, polyurethane elastomer with the following physical properties: tensile strength 1,550 psi, elongation 500%, hardness (shore A) 55. Extraction tests with deionized water exhibit less than 0.1% extractables.

The water absorptivity of the elastomer is determined by weight difference between a dry film and a wet film after immersion in water for six hours. The elastomer of this example absorbs about 50% water.

EXAMPLE II

The procedure of Example I is repeated except that isophorone diisocyanate (IPDI) (2.0 equiv.) is used in place of the TMDI. The resultant liquid oligomer has a viscosity of 45,000 centipoise at room temperature and thus requires slight heating, i.e. to a temperature of about 40° C., to facilitate subsequent mixing with the photoinitiator.

A clear 0.030" film is cast from the oligomer-photoinitiator composition and cures by ultraviolet radiation exposure for 30 seconds. The resultant elastomer has the following physical properties: tensile strength 1,450 psi, elongation 450%, hardness (shore A) 55. It is capable of absorbing up to about 45% water. Extraction tests with deionized water exhibit less than 0.1% extractables.

EXAMPLE III

The procedure of Example I is repeated except that 4,4'-dicyclohexylmethane diisocyanate (H12MDI) (2.0 equiv.) is used in place of the TMDI. The resultant oligomer is very viscous having a viscosity of over 50,000 centipoise at room temperature and thus requires heating to a temperature of about 50° C. to maintain sufficient liquidity to incorporate the photoinitiator. This particular oligomer would not be suitable for use with especially heat-sensitive medications which would be damaged by exposure to the slightly elevated temperature.

A clear 0.030" film is cast from the oligomer-photoinitiator composition and cures by exposure to ultraviolet radiation for 60 seconds. The resultant elastomer has the following physical properties: tensile strength 1,400 psi, elongation 400%, hardness (shore A) 60. It is capable of absorbing up to about 40% water. Extraction tests with deionized water exhibit less than 0.1% extractables.

COMPARATIVE EXAMPLE A

The procedure of Example I is repeated except that an aromatic diisocyanate, toluene diisocyanate (TDI) (2.0 equiv.), is used in place of the TMDI. The resultant oligomer is a semi-solid, for which a viscosity could not be determined, which does not become liquid until heated to a temperature of about 60° C.

A clear 0.030" film is cast from the oligomer-photoinitiator composition and curing by exposure to ultraviolet radiation fails to produce any cure even after 6 minutes of exposure. A second film only 0.004" thick is cast. It does cure by uv exposure, but only after more than 5 minutes of ultraviolet radiation. Aromatic diisocyanates absorb too much of the ultraviolet radiation to produce elastomers which can be cured within a commercially reasonable amount of time. No physical properties are obtained because of the excessive cure time.

COMPARATIVE EXAMPLE B

The procedure of Example I is repeated except that another aromatic diisocyanate, 4,4'-diphenylmethane diisocyanate (MDI) (2.0 equiv.), is used in place of the TMDI. The resultant oligomer is a solid at room temperature and does not becoming fully liquid until heated to a temperature of about 80° C.

A slightly yellow 0.030" film cast from the oligomer-photoinitiator composition does not cure after exposure to ultraviolet radiation even for more than 6 minutes. A thinner film only 0.003" thick does cure, but only after more than 5 minutes exposure to the ultraviolet radiation. No physical properties are obtained due to the excessive cure time.

COMPARATIVE EXAMPLE C

The procedure of Example I is repeated except that the polyethylene glycol is replaced by polypropylene glycol (1.0 equiv.). The resulting oligomer is viscous, having a viscosity of 45,000 centipoise at room temperature and requiring a temperature of 45° C. to maintain sufficient liquidity to readily incorporate the photoinitiator.

A clear 0.030" film is cast from the oligomer-photoinitiator composition and is cured by exposure to ultraviolet radiation, but only after more than 3 minutes of exposure.

The resultant material is elastomeric, but is not hydrophilic. Rather, it is considered hydrophobic since it absorbs less than 3% water. It is unsuitable for use in the delivery of water-soluble medications.

EXAMPLE IV

The procedure of Example I is repeated except that a polyethylene glycol of molecular weight 2000 is used. The resultant oligomer is more viscous than that of Example I, exhibiting a viscosity of about 35,000 centipoise at room temperature. Incorporation of the photoinitiator is performed in the absence of any heating procedure.

A 0.030" film is cast and cures within 60 seconds. The properties of the film are essentially the same as those of the film of Example I.

COMPARATIVE EXAMPLE D

The procedure of Example IV is repeated except that the molecular weight of the polyethylene glycol used is 3500 Daltons. The resultant oligomer is solid, almost wood-like and would require excessive heating to make it sufficiently liquid to incorporate the photoinitiator.

EXAMPLE V

The procedure of Example I is repeated except that the polyethylene glycol (1,000 MW) is replaced by polyethylene oxide diamine having a molecular weight of about 1000 Daltons. The diamine is prepared by a two-step procedure of (i) bromination of polyethylene glycol by heating with hydrogen bromide at 60° C. for 4 hours, followed by (ii) amination by reaction with excess ammonia at room temperature for 2 hours. The resulting oligomer is of similar viscosity to that of Example I.

A 0.030" cast film of the oligomer-photoinitiator combination cures after less than 20 seconds of ultraviolet radiation exposure. The resultant film exhibits properties essentially similar to those of the film of Example I.

EXAMPLE VI

To demonstrate the effectiveness of the urethane elastomers at dispensing a highly volatile water-insoluble, lipophilic medication, the procedure of Example I is repeated to prepare an oligomer containing 5% by weight $-CH_2CH_2O-$ groups by using a mixture of polyethylene glycol and polypropylene glycol as the bifunctional component. Thereafter, 2% of the photoinitiator and 20% methyl salicylate is uniformly mixed therein and an about 100 micron thick film is cast from the mixture. The resultant film cures by exposure to ultraviolet radiation for about 30 seconds.

The release kinetics of the methyl salicylate are determined by simple weight difference, using a precision Mettler TM scale capable of weighing +/−0.0001 g. The film is placed in a circulating air oven maintained at 38° C. and the amount of methyl salicylate eluted in milligrams per square centimeter of film is determined at various time intervals. The results are:

| Elapsed Time (hrs) | Eluted conc (mg/sq · cm) |
|---|---|
| 4 | 56 |
| 8 | 85 |
| 12 | 113 |
| 16 | 143 |
| 24 | 174 |

The release kinetics of the methyl salicylate follow substantially constant, zero order kinetics for the entire 24 hour period.

EXAMPLE VII

The procedure of Example VI is repeated to test the release kinetics of methyl nicotinate, a water-soluble, lipophobic rubefacient, into an aqueous solution. Methyl nicotinate is selected as the test medication since it is freely soluble in water. Moreover, it displays an absorption maxima at 267 nanometers, thus making it particularly suitable for analysis by means of UV spectrophotometric methods, rather than weight difference.

An oligomer is prepared as in Example I but containing 75% by weight $-CH_2CH_2O-$ groups and the methyl nicotinate is added thereto as in Example VI. Suitable films are cast from the composition and cured by exposure to ultraviolet radiation. Samples of the film are die cut to 2.0 cm in diameter and placed on standard Franz cells containing 10 ml of deionized water. The water is withdrawn at predetermined intervals and analyzed for methyl nicotinate and fresh deionized water added to the cells to insure maintainance of sink conditions at all times.

The eluted concentrations of the methyl nicotinate in milligrams per square centimeter of film as a function of elapsed time are found to be:

| Elapsed Time (hrs) | Eluted conc (mg/sq. cm) |
|---|---|
| 4 | 10 |
| 8 | 18 |
| 12 | 27 |
| 16 | 35 |
| 20 | 45 |
| 24 | 54 |

The release kinetics of the methyl nicotinate follow essentially constant, zero order kinetics for the entire 24 hour period.

What is claimed is:

1. A hydrophilic polyurethane elastomer which has been cured by exposure to actinic radiation in the presence of at least one photoinitiator containing a polymerizable group said cured elastomer containing less than about 0.5 weight % extractables as prepared without the need to perform a leaching operation on the cured elastomer.

2. The elastomer of claim 1 wherein it contains less than about 0.1 weight % extractables.

3. The elastomer of claim 1 which has been non-exothermically cured by exposure to ultraviolet radiation.

4. The elastomer of claim 3 wherein the ultraviolet radiation exposure is for less than about 120 seconds.

5. The elastomer of claim 3 wherein the ultraviolet radiation exposure is for less than about 60 seconds.

6. The elastomer of claim 1 comprising a cured reaction product having at least about 5 weight percent poly(ethyleneoxide) groups of the formula $-CH_2CH_2O-$ and prepared from an oligomer of an aliphatic diisocyanate, a bifunctional component having two terminal groups each of which contains an active hydrogen, and a chain capping monomer which contains both an active hydrogen and a polymerizable vinyl group, and a photoinitiator which contains a polymerizable vinyl group.

7. The elastomer of claim 6 wherein the bifunctional component is a polyethylene glycol having a molecular weight of about 500 to less than about 3000 Daltons.

8. The elastomer of claim 7 wherein the polyethylene glycol has a molecular weight of about 750 to about 2500 Daltons.

9. The elastomer of claim 7 wherein the polyethylene glycol has a molecular weight of about 900 to about 1500 Daltons.

10. The elastomer of claim 7 wherein at least 20% by weight of the elastomer is polyethylene glycol.

11. The elastomer of claim 6 wherein the aliphatic diisocyanate is of the formula $OCN-R-NCO$ wherein R is selected from the group consisting essentially of aliphatic, aliphatic-alicyclic and aliphatic-aromatic hydrocarbon compounds containing from about 4 to about 26 carbon atoms.

12. The elastomer of claim 11 wherein the aliphatic diisocyanate is selected from the group consisting essentially of tetramethylene diisocyanate, hexamethylene diisocyanate, trimethylhexamethylene diisocyanate, dimer acid diisocyanate, isophorone diisocyanate, hydrogenated diphenylmethane diisocyanate, methylene di(cyclohexyl isocyanate), metaxylene diisocyanate, diethylbenzene diisocyanate, decamethylene 1,10-diisocyanate, cyclohexylene 1,2-diisocyanate, and cyclohexylene 1,4-diisocyanate.

13. The elastomer of claim 6 wherein the chain capping monomer contains one vinyl group.

14. The elastomer of claim 6 wherein the chain capping monomer is hydroxyethyl acrylate or hydroxyethyl methacrylate.

15. The elastomer of claim 6 wherein the photoinitiator comprises about 1 to about 5 weight percent based on the weight of the oligomer.

16. The elastomer of claim 15 wherein the photoinitiator comprises about 1.5 to about 4 weight percent based on the weight of the oligomer.

17. The elastomer of claim 1 wherein the photoinitiator is selected from the group consisting of benzil ketals, benzoin ethers, and aromatic ketones, which have been modified to contain a polymerizable vinyl group.

18. The elastomer of claim 1 wherein the photoinitiator is selected from the group consisting essentially of (i) 4-(2-acryloyloxyethoxy)-phenyl-2-hydroxy-2-propylketone, (ii) 4-[2-(3-triethoxysilylpropoxy)]phenyl-2-hydroxy-2-propylketone, (iii) 4-(2-azidoethoxy)-phenyl-2-hydroxy-2-propylketone, (iv) 4-(2-aminoethoxy)phenyl-2-hydroxy-2-propylketone.

19. The elastomer of claim 15 wherein the photoinitiator is 4-(2-acryloyl-oxyethoxy)-phenyl-2-hydroxy-2-propylketone.

20. The elastomer of claim 1 wherein the elastomer is cured through terminal vinyl groups on a polyurethane oligomer.

21. The elastomer of claim 1 wherein said elastomer is cured by incorporation of about 1 to about 5 weight percent of a photoinitiator containing a hydroxyl group and a vinyl group and then exposing it to ultraviolet radiation.

22. The elastomer of claim 21 wherein the photoinitiator is used in amount of about 1.5 to about 4 weight percent.

23. The elastomer of claim 21 wherein the photoinitiator is 4-(2-acryloyl-oxyethoxy-)-phenyl-2-hydroxy-2-propylketone.

24. A hydrophilic polyurethane elastomer according to claim 1, wherein the elastomer is cured at about room temperature.

25. A process for preparing a drug delivery system capable of delivering a drug through the unbroken skin or mucosa of a patient which comprises:

(A) preparing an —NCO-free reaction product having at least about 5 weight percent poly(ethyleneoxide) groups of the formula $-CH_2CH_2O-$ from an aliphatic diisocyanate, a bifunctional component having two terminal groups each of which contains an active hydrogen, and a chain capping monomer which contains both an active hydrogen and a polymerizable vinyl group;

(B) admixing said reaction product with (i) a photoinitiator which contains a polymerizable vinyl group and (ii) a drug;

(C) forming the admixture into a film having a thickness of about 0.010 to about 0.050 inches; and (D) curing said film at about room temperature by exposing it to ultraviolet radiation for less than about 2 minutes.

26. The process of claim 25 wherein the bifunctional component comprises a polyethylene glycol having a molecular weight of about 500 to less than about 3000 Daltons.

27. The process of claim 26 wherein the polyethylene glycol has a molecular weight of about 750 to about 2500 Daltons.

28. The process of claim 25 wherein the aliphatic diisocyanate is of the formula OCN—R—NCO wherein R is selected from the group consisting essentially of aliphatic, aliphatic-alicyclic and aliphatic-aromatic hydrocarbon compounds containing from about 4 to about 26 carbon atoms.

29. The process of claim 28 wherein the aliphatic diisocyanate is selected from the group consisting essentially of tetramethylene diisocyanate, hexamethylene diisocyanate, trimethylhexamethylene diisocyanate, dimer acid diisocyanate, isophorone diisocyanate, hydrogenated diphenylmethane diisocyanate, methylene di(cyclohexyl isocyanate), metaxylene diisocyanate, diethylbenzene diisocyanate, decamethylene 1,10-diisocyanate, cyclohexylene 1,2-diisocyanate, and cyclohexylene 1,4-diisocyanate.

30. The process of claim 25 wherein the chain capping monomer is hydroxyethyl acrylate or hydroxyethyl methacrylate.

31. The process of claim 25 wherein the photoinitiator is selected from the group consisting of benzil ketals, benzoin ethers, and aromatic ketones, which have been modified to contain a polymerizable vinyl group.

32. The process of claim 31 wherein the photoinitiator is 4-(2-acryloyl-oxyethoxy)-phenyl-2-hydroxy-2-propylketone.

33. The process of claim 25 wherein said drug is selected from the group consisting essentially of pharmaceuticals, bacteriostats, viruscides, antibiotics, antifungal agents, topical anaesthetics, growth factors, skin softeners, anti-acne medications, external anaesthetics, and cosmetics.

34. The process of claim 25 further comprising coating one surface of said film with a pressure sensitive adhesive.

35. A drug delivery system suitable for delivering a medication to a patient through its unbroken skin or mucosa which is prepared by (i) preparing a mixture of a medication, a liquid oligomer having two terminal vinyl groups, and a photoinitiator having a polymerizable vinyl group, (ii) forming the mixture into a shaped body, and (iii) exposing the shaped body to ultraviolet radiation for less than about 2 minutes.

36. The drug delivery system of claim 35 wherein the liquid oligomer comprises at least about 5 weight percent poly(ethyleneoxide) groups of the formula $—CH_2CH_2O—$ and is prepared from an aliphatic diisocyanate, a bifunctional component having two terminal groups each of which contains an active hydrogen, and a chain capping monomer which contains both an active hydrogen and a polymerizable vinyl group.

37. The drug delivery system of claim 36 wherein the bifunctional component is a polyethylene glycol having a molecular weight of about 500 to less than about 3000 Daltons.

38. The drug delivery system of claim 37 wherein the polyethylene glycol has a molecular weight of about 750 to about 2500 Daltons.

39. The drug delivery system of claim 37 wherein the polyethylene glycol has a molecular weight of about 900 to about 1500 Daltons.

40. The drug delivery system of claim 37 wherein at least 20% by weight of the liquid oligomer is polyethylene glycol.

41. The drug delivery system of claim 36 wherein the diisocyanate is of the formula OCN—R—NCO wherein R is selected from the group consisting essentially of aliphatic, aliphatic-alicyclic and aliphatic-aromatic hydrocarbon compounds containing from about 4 to about 26 carbon atoms.

42. The drug delivery system of claim 41 wherein the diisocyanate is selected from the group consisting essentially of tetramethylene diisocyanate, hexamethylene diisocyanate, trimethylhexamethylene diisocyanate, dimer acid diisocyanate, isophorone diisocyanate, hydrogenated diphenylmethane diisocyanate, methylene di(cyclohexyl isocyanate), metaxylene diisocyanate, diethylbenzene diisocyanate, decamethylene 1,10-diisocyanate, cyclohexylene 1,2-diisocyanate, and cyclohexylene 1,4-diisocyanate.

43. The drug delivery system of claim 36 wherein the chain capping monomer contains one vinyl group.

44. The drug delivery system of claim 36 wherein the chain capping monomer is hydroxyethyl acrylate or hydroxyethyl methacrylate.

45. The drug delivery system of claim 36 wherein the photoinitiator comprises about 1 to about 5 weight percent of the oligomer.

46. The drug delivery system of claim 35 wherein the photoinitiator comprises about 1.5 to about 4 weight percent of the oligomer.

47. The drug delivery system of claim 35 wherein the photoinitiator is selected from the group consisting of benzil ketals, benzoin ethers, and aromatic ketones, which have been modified to contain a polymerizable vinyl group.

48. The drug delivery system of claim 35 wherein the photoinitiator is 4-(2-acryloyl-oxyethoxy)-phenyl-2-hydroxy-2-propylketone.

* * * * *